(12) United States Patent
Zhang et al.

(10) Patent No.: US 11,844,916 B2
(45) Date of Patent: Dec. 19, 2023

(54) EAR IRRIGATION DEVICE

(71) Applicant: Ningbo Albert Novosino Co., Ltd., Zhejiang (CN)

(72) Inventors: Yonggui Zhang, Zhejiang (CN); Haibo Hu, Zhejiang (CN)

(73) Assignee: NINGBO ALBERT NOVOSINO CO., LTD., Zhejiang (CN)

( * ) Notice: Subject to any disclaimer, the term of this patent is extended or adjusted under 35 U.S.C. 154(b) by 265 days.

(21) Appl. No.: 17/237,074

(22) Filed: Apr. 22, 2021

(65) Prior Publication Data

US 2022/0203018 A1 Jun. 30, 2022

(30) Foreign Application Priority Data

Dec. 30, 2020 (CN) .......................... 202023345858.1

(51) Int. Cl.
 *A61M 3/02* (2006.01)
(52) U.S. Cl.
 CPC ........ *A61M 3/0283* (2013.01); *A61M 3/0258* (2013.01); *A61M 2210/0662* (2013.01)
(58) Field of Classification Search
 CPC .............. A61M 3/0283; A61M 3/0258; A61M 2210/0662; A61M 3/0275; A61M 2039/242; A61M 1/774; A61M 1/77; A61M 1/76; A61C 17/0202; A61C 17/028; A61C 17/02; A61C 1/0092; Y10T 74/18056
 See application file for complete search history.

(56) References Cited

U.S. PATENT DOCUMENTS

| 3,862,807 A | * | 1/1975 | Doden .................. F16C 11/069 403/135 |
| 5,246,367 A | | 9/1993 | Ito et al. |
| 5,833,675 A | * | 11/1998 | Garcia ................ A61M 3/0262 604/290 |
| 2012/0277678 A1 | | 11/2012 | Taylor et al. |

(Continued)

FOREIGN PATENT DOCUMENTS

| CN | 209499949 U | 10/2019 |
| CN | 111643205 A | 9/2020 |
| GB | 2318736 A | 5/1998 |

OTHER PUBLICATIONS

Combined Search and Examination Report of counterpart British patent application No. GB2112439.1 dated Dec. 6, 2021.

*Primary Examiner* — Brandy S Lee
*Assistant Examiner* — Phoebe Anne Staton
(74) *Attorney, Agent, or Firm* — COOPER LEGAL GROUP, LLC

(57) ABSTRACT

An ear irrigation device includes a water reservoir, a water inlet chamber, a water inlet assembly communicating with the water inlet chamber and a water outlet assembly communicating with the water inlet chamber. A piston is inserted at one end of the water inlet chamber, the piston and an interior of the water inlet chamber form a chamber, a recess is formed on a side of the piston away from the chamber, a rotor is rotatably connected in the recess, the rotor is connected with a link, an end of the link away from the rotor is connected with an eccentric rotating assembly, one end of the water inlet assembly communicates with the water reservoir, a check valve is arranged in the water inlet assembly, and another check valve is arranged in the water outlet assembly.

9 Claims, 10 Drawing Sheets

(56) References Cited

U.S. PATENT DOCUMENTS

| | | | |
|---|---|---|---|
| 2016/0151133 A1* | 6/2016 | Luettgen | F04B 53/14 |
| | | | 433/80 |
| 2017/0049530 A1* | 2/2017 | Cacka | A61H 13/005 |
| 2018/0153666 A1 | 6/2018 | Snyder et al. | |
| 2020/0208548 A1* | 7/2020 | Murrish | F01M 1/08 |
| 2020/0276003 A1 | 9/2020 | Luettgen et al. | |

* cited by examiner

EAR IRRIGATION DEVICE

CROSS-REFERENCE TO RELATED APPLICATION

This application is based on and claims the priority benefits of China application No. 202023345858.1, filed on Dec. 30, 2020. The entirety of the above-mentioned patent application is hereby incorporated by reference herein and made a part of this specification.

BACKGROUND

Technical Field

The present application relates to the field of medical instruments, and in particular, to an ear irrigation device.

Description of Related Art

Irrigation of the external auditory canal refers to irrigating an ear with warm physiological saline to remove soft cerumen and small cerumen fragments, tiny foreign materials or softening impacted cerumen which are not easy to remove from the deep part of the external auditory canal, with the need of using an ear irrigator, warm physiological saline, cotton swab, or the like.

In the related art, an ear washer reservoir is generally used for introducing water into an auditory canal, and the water is pumped into the auditory canal by pressing the pressing handle of the ear washer reservoir by hand. Therefore, different pressing handles are required for the user, and the operation is troublesome. However, if a general electric irrigation device is adopted to pump water into the auditory canal, the tympanic membrane in the auditory canal will be subjected to an impact since the water flow of the irrigating water is continuous, thereby causing discomfort to the user.

SUMMARY

In order to reduce the impact of the water flow of an electric irrigation device on the auditory canal, the present application provides an ear irrigation device.

In one embodiment, an ear irrigation device includes a water reservoir, a water inlet chamber, a water inlet assembly and a water outlet assembly. The water inlet assembly communicates with the water inlet chamber, the water outlet assembly communicates with the water inlet chamber. One end of the water inlet chamber is provided with a slidably engaged piston by insertion, the piston and an interior of the water inlet chamber form a chamber, a recess is formed on a side of the piston facing away from the chamber, and a rotor is rotatably connected in the recess. The rotor is connected with a link, an end of the link away from the rotor is connected with an eccentric rotating assembly which drives one end of the link connecting the rotor to reciprocate in the direction of the chamber. One end of the water inlet assembly communicates with the water reservoir, a check valve in unidirectional communication with the interior of the water inlet chamber is arranged in the water inlet assembly, and another check valve in unidirectional communication with the outside of the water inlet chamber is arranged in the water outlet assembly.

By adopting the above technical solution, when the eccentric rotating assembly drives the piston to move in a direction away from the chamber formed by the water inlet chamber through the rotor on the link, a negative pressure is generated in the chamber. Due to the unidirectional flow function of the check valve, the water outlet assembly is closed, and then the water inlet assembly is communicated, and the water inlet assembly introduces water in the water reservoir into the chamber. When the piston moves towards the chamber, the water inlet assembly is closed, the water outlet assembly is communicated, and water in the chamber flows out through the water outlet assembly. Therefore, when the piston reciprocates, the chamber is repeatedly switched between the water inlet action and the water outlet action, so that water intermittently flows out, thus avoiding the impact of continuous water flow on the tympanic membrane.

Optionally, the eccentric rotating assembly includes a rotating disk, an eccentric ring, a driving ring and a rotating motor. A rotating shaft penetrates through an axial center of the rotating disk, the eccentric ring is eccentrically connected to a side surface of the rotating disk, the rotating shaft is located in a space surrounded by the eccentric ring, the driving ring is coaxially sleeved outside the eccentric ring, the driving ring is connected to the link, a conical gear ring is coaxially connected with a side edge of the rotating disk, and a driving shaft of the rotating motor is coaxially connected with a conical gear meshed with the conical gear ring.

By adopting the above technical solution, the rotating motor drives the conical gear to rotate the meshed conical gear ring, so as to rotate the eccentric ring on the rotating disk, and the eccentric ring in turn drives the driving ring to move up and down with left and right shaking. The left and right shaking of the driving ring are converted into sliding between the rotor and the recess, and the up-down movement of the driving ring are converted into a reciprocating movement of the piston towards the chamber.

Optionally, the ear irrigation device further includes a base and an end cover, the base and the end cover are connected to form a cavity enclosing the rotating disk, the eccentric ring and the driving ring. A first pivotal groove is formed in a side surface of the base facing the end cover, a second pivotal groove is formed in a side surface of the end cover facing the base, and two ends of the rotating shaft abut against an inner bottom wall of the first pivotal groove and an inner bottom wall of the second pivotal groove, respectively.

By adopting the above technical solution, the base and the end cover form the cavity to protect the movement of the rotating disk, the eccentric ring and the driving ring, and the first pivotal groove and the second pivotal groove axially limit the rotating shaft.

Optionally, an inner wall of the recess is provided with a radially protruded ring, and the protruded ring abuts against the rotor and prevents the rotor from disengaging from the recess.

By adopting the above technical solution, the protruded ring prevents the rotor from disengaging from the recess.

Optionally, an annular groove is circumferentially formed in the side wall of the piston, and a sealing ring is embedded in the annular groove.

By adopting the above technical solution, the sealing ring improves the sealing property between the side wall of the piston and the inner wall of the water inlet chamber, and avoids air leakage or water leakage between the side wall of the piston and the inner wall of the water inlet chamber.

Optionally, the water inlet assembly includes a first water inlet connector, a second water inlet connector, a first water inlet pipe, a second water inlet pipe and a closure plug. The first water inlet connector communicates with the water inlet chamber, the first water inlet pipe communicates with the first water inlet connector, one end of the first water inlet pipe away from the first water inlet connector communicates with the second water inlet connector, one end of the second water inlet connector away from the first water inlet pipe is circumferentially sleeved with the closure plug. The closure plug is axially formed with a water passage hole communicating with the first water inlet pipe, the second water inlet pipe is inserted into one end of the water passage hole away from the first water inlet pipe, one open end of the water reservoir is sleeved on a circumferential side wall of the closure plug, one end of the second water inlet pipe away from the closure plug is close to an inner bottom wall of the water reservoir, and the closure plug is axially formed with a ventilation hole communicating with the water reservoir.

By adopting the above technical solution, the circumferential side wall of the closure plug is snap connected in the inner wall of the water reservoir, to avoid the water in the water reservoir from leaking out of the reservoir opening. The ventilation hole equalizes the air pressure in the water reservoir pumps water, thereby avoiding the difficulty of pumping water due to negative pressure generated in the water reservoir.

Optionally, the water outlet assembly includes a water outlet connector, a first water outlet pipe and a second water outlet pipe, the water outlet connector communicates with the water inlet chamber, the first water outlet pipe communicates with the water outlet connector, and the second water outlet pipe communicates with one end of the first water outlet pipe away from the water outlet connector.

By adopting the above technical solution, the water outlet assembly is divided into a separate water outlet connector, a first water outlet pipe and a second water outlet pipe, which can be assembled, so as to facilitate the processing of the water outlet assembly.

Optionally, the check valve includes a spring, a ball head and a water passage base allowing water to pass through, and two ends of the spring are respectively connected with the water passage base and the ball head.

By adopting the above technical solution, the ball head closes the water inlet assembly and the water outlet assembly, and the spring provides a force for the ball head to close the water inlet assembly and the water outlet assembly.

Optionally, one end of the second water outlet pipe away from the first water outlet pipe is detachably connected with an irrigation nozzle.

By adopting the above technical solution, the irrigation nozzle is replaceable, and the ear irrigation device is more hygienic to use.

Optionally, an ear cover is circumferentially connected with the side wall of the irrigation nozzle.

By adopting the above technical solution, the ear cover may receive water flowing out of the auditory canal and gather the water collectively.

In summary, the present application provides at least one of the following advantages:

The eccentric rotating assembly drives the piston to reciprocate, so that water intermittently flows out, thus avoiding the impact of continuous water flow on the tympanic membrane.

DESCRIPTION OF THE EMBODIMENTS

This application is described in detail below in combination with FIGS. 1-10.

Figure 1:
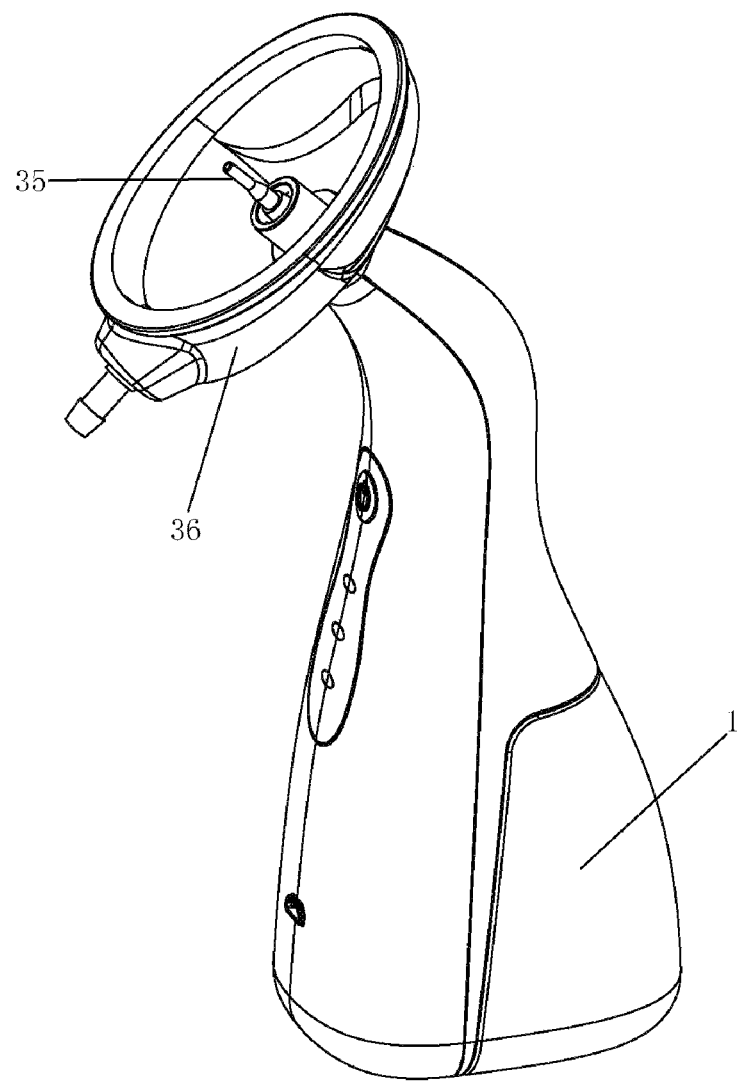
FIG. 1 is a schematic diagram showing an overall structure of an ear irrigation device according to an embodiment of the present application.

Embodiments of the present application disclose an ear irrigation device. Referring to FIG. 1, the ear irrigation device includes a water reservoir 1, an irrigation nozzle 35 and an ear cover 36. The ear cover 36 is circumferentially connected with the side wall of the irrigation nozzle 35. When in use, the ear is covered with the ear cover 36, the irrigation nozzle 35 is inserted into the external auditory canal, and water is introduced from the water reservoir 1 into the external auditory canal through the irrigation nozzle 35.

Figure 2:
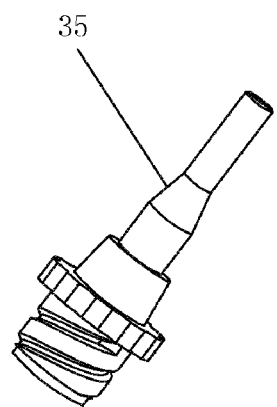
FIG. 2 is a structural schematic diagram of an irrigation nozzle according to an embodiment of the present application.

Referring to FIG. 2, the irrigation nozzle 35 has screw threads formed on an outer side wall at the end thereof for connection.

Figure 3:
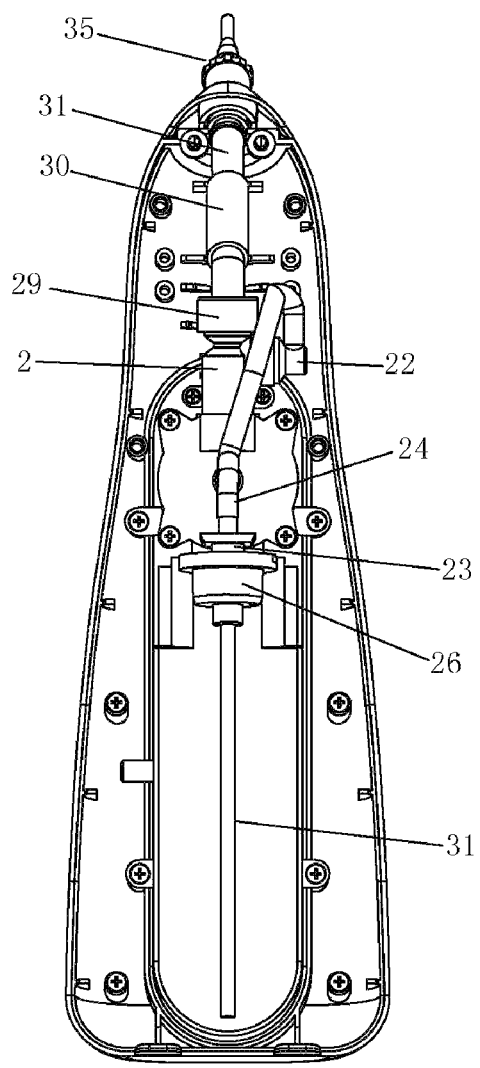
FIG. 3 is a schematic diagram showing an internal structure of an ear irrigation device according to an embodiment of the present application.
Figure 4:
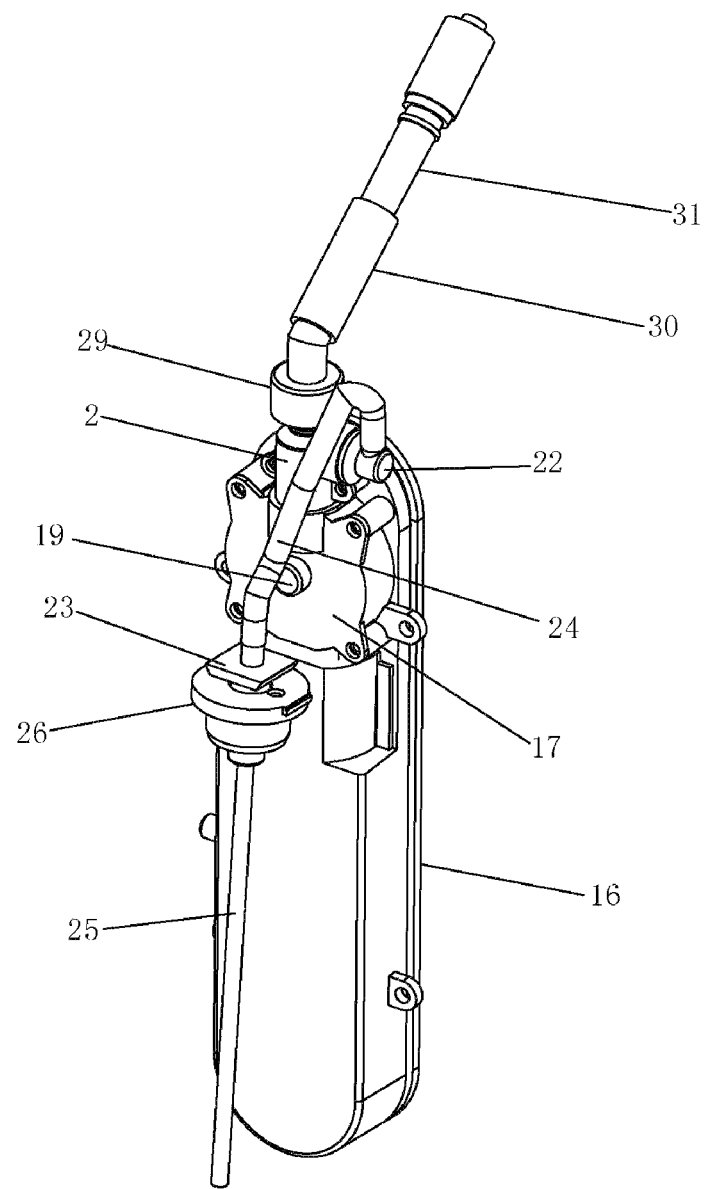
FIG. 4 is a structural schematic diagram of an irrigation nozzle, with the housing being removed, according to an embodiment of the present application.

Referring to FIGS. 3 and 4, a water inlet chamber 2, a water inlet assembly and a water outlet assembly are arranged within a housing of the ear irrigation device. The water inlet assembly communicates with the water inlet chamber 2, and the water outlet assembly communicates with the water inlet chamber 2. One end of the water inlet assembly away from the water inlet chamber 2 is inserted into the bottom of the water reservoir 1, and one end of the water outlet assembly away from the water inlet chamber 2 communicates with the irrigation nozzle 35.

Referring to FIG. 4, the water outlet assembly includes a water outlet connector 29, a first water outlet pipe 30 and a second water outlet pipe 31, the water outlet connector 29 communicates with the water inlet chamber 2, the first water outlet pipe 30 communicates with the water outlet connector 29, and the second water outlet pipe 31 communicates with one end of the first water outlet pipe 30 away from the water outlet connector 29. The irrigation nozzle 35 communicates with one end of the second water outlet pipe 31 away from the first water outlet pipe 30. In some embodiments, the water outlet connector 29 communicates with the water inlet chamber 2 in such a way that the water outlet connector 29 is integrally formed with the water inlet chamber 2, and a through hole communicating with the water inlet chamber 2 is formed along the axis of the water outlet connector 29. The first water outlet pipe 30 communicates with the water outlet connector 29 in such a way as to extend an integrally formed hollow pipe body from the water outlet connector 29, and the first water outlet pipe 30 is coaxially sleeved on the pipe body extending from the water outlet connector 29. The second water outlet pipe 31 communicates with one end of the first water outlet pipe 30 away from the water outlet connector 29 in such a way that one end of the first water outlet pipe 30 is sleeved at one end of the second water outlet pipe 31. The irrigation nozzle 35 communicates with one end of the second water outlet pipe 31 away from the first water outlet pipe 30 in such a way that the screw thread on the outer side wall of the irrigation nozzle 35 is in threaded connection with the inner wall of the second water outlet pipe 31.

Referring to FIG. 4, the water inlet assembly includes a first water inlet connector 22, a second water inlet connector 23, a first water inlet pipe 24, a second water inlet pipe 25 and a closure plug 26. The first water inlet connector 22 communicates with the water inlet chamber 2, the first water inlet pipe 24 communicates with the first water inlet connector 22. One end of the first water inlet pipe 24 away from the first water inlet connector 22 communicates with the second water inlet connector 23. One end of the second water inlet connector 23 away from the first water inlet pipe 24 is circumferentially sleeved with a closure plug 26. In some embodiments, the first water inlet connector 22 communicates with the water inlet chamber 2 in such a way that the first water inlet connector 22 is integrally formed with the water inlet chamber 2, and the first water inlet connector 22 is axially formed with a through hole communicating with the water inlet chamber 2. The first water inlet pipe 24 communicates with the first water inlet connector 22 in such a way that a pipe body communicating with the first water inlet connector 22 is integrally formed on the first water inlet connector 22, and the first water inlet pipe 24 is coaxially sleeved on the pipe body integrally formed on the first water inlet connector 22. One end of the first water inlet pipe 24 away from the first water inlet connector 22 communicates with the second water inlet connector 23 in such a way that a pipe body is integrally formed at an upper end of the second water inlet connector 23, and the first water inlet pipe 24 is sleeved on the pipe body integrally formed with the second water inlet connector 23.

Figure 8:
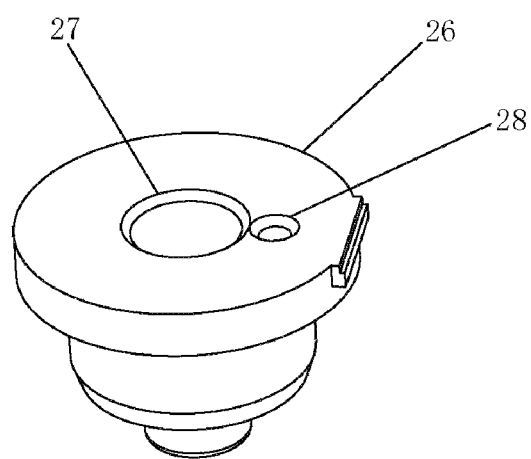
FIG. 8 is a structural schematic diagram of a closure plug according to an embodiment of the present application.

Referring to FIG. 8, the closure plug 26 is axially formed with a water passage hole 27 communicating with the first water inlet pipe 24, and the closure plug 26 is axially formed with a ventilation hole 28 spaced from the water passage hole 27. The second water inlet pipe 25 is inserted into one end of the water passage hole 27 away from the first water inlet pipe 24, an opening of the water reservoir 1 is sleeved on a circumferential side wall of the closure plug 26, one end of the second water inlet pipe 25 away from the closure plug 26 is close to an inner bottom wall of the water reservoir 1. In some embodiments, the closure plug 26 is made of rubber, and when an open end of the water reservoir 1 is circumferentially sleeved on the side wall of the closure plug 26, the inner wall of the reservoir opening of the water reservoir 1 is in close contact with the outer side wall of the closure plug 26, thereby preventing water from leaking out of the junction between the water reservoir 1 and the closure plug 26. The upper ventilation hole 28 of the closure plug 26 plays a role of equalizing the air pressure with the outside, thereby avoiding the difficulty of pumping water due to negative pressure generated in the water reservoir 1.

Figure 5:
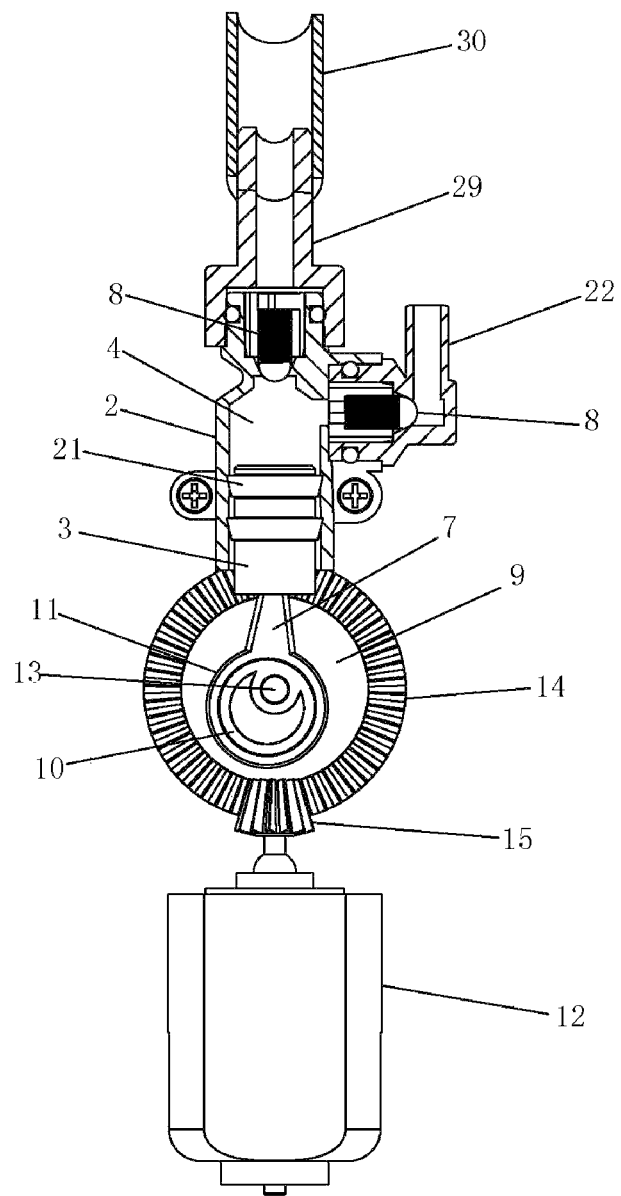
FIG. 5 is a partial sectional view of an ear irrigation device according to an embodiment of the present application.
Figure 10:
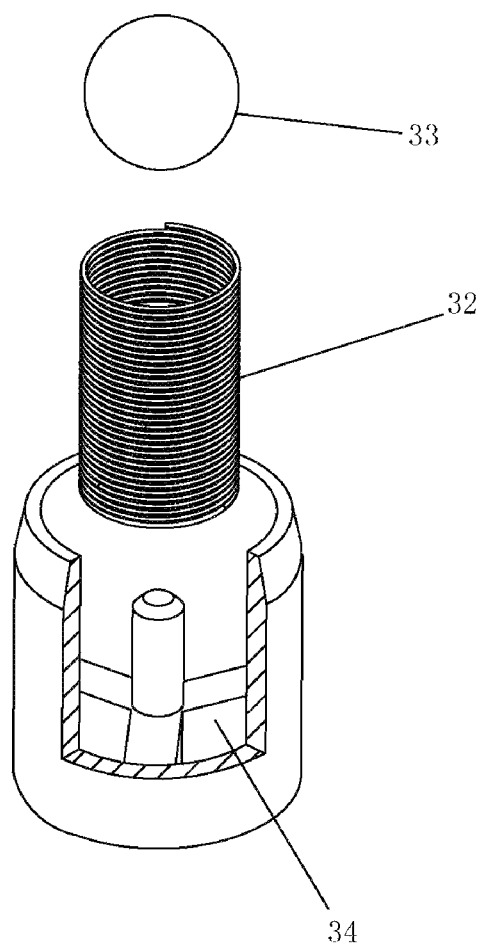
FIG. 10 is an exploded view of a check valve according to an embodiment of the present application.

Referring to FIG. 5, one end of the water inlet chamber 2 away from the water outlet connector 29 and the first water inlet connector 22 is inserted into and slidably connected with a piston 3, and a cavity 4 is formed between the piston 3 and the water inlet chamber 2. Check valves 8 are arranged both at the junction between the water outlet connector 29 and the water inlet chamber 2, and at the junction between the first water inlet connector 22 and the water inlet chamber 2. In some embodiments, the check valve 8 in the first water inlet connector 22 in unidirectional communication with the interior of the water inlet chamber 2, and the check valve 8 in the water outlet connector 29 in unidirectional communication with the outside of the water inlet chamber 2. Referring to FIG. 10, the check valve 8 includes a spring 32, a ball head 33 and a water passage base 34 allowing water to pass through, and two ends of the spring 32 are respectively connected with the water passage base 34 and the ball head 33. The water passage base 34 is formed by three rods extending radially from one point, a positioning rod is connected to the center of the water passage base 34, and the positioning rod is located on the axis of the spring 32. Referring to FIG. 5, the ball head 33 of the check valve 8 in the first water inlet connector 22 closes the hollow pipe body extending from the first water inlet connector 22. The ball head 33 of the check valve 8 at the junction between the water outlet connector 29 and the water inlet chamber 2 closes the hole communicating with the water inlet chamber 2 and the water outlet connector 29. In some embodiments, the check valve 8 can achieve a unidirectional flow function at any position in the water inlet assembly and the water outlet assembly, so the check valve 8 can be within the water inlet assembly and the water outlet assembly.

Figure 6:
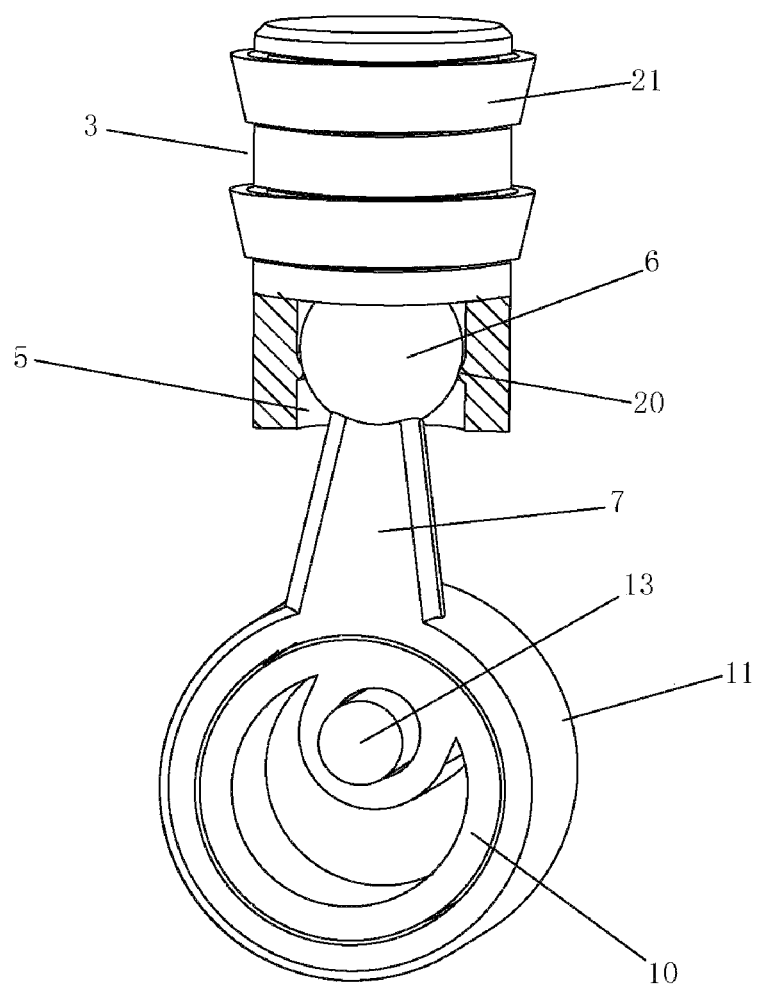
FIG. 6 is a sectional view of a piston according to an embodiment of the present application.
Figure 7:
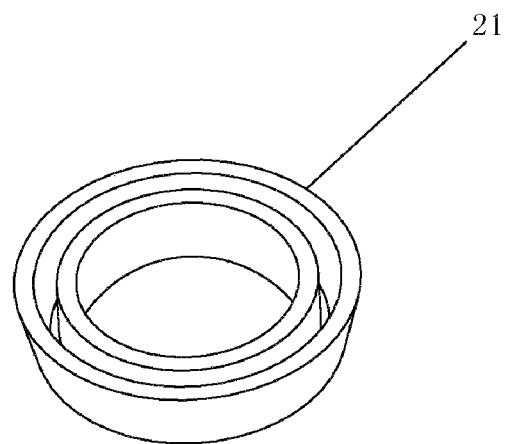
FIG. 7 is a structural schematic diagram of a sealing ring according to an embodiment of the present application.

With reference to FIGS. 5 and 6, a recess 5 is formed at an end of the piston 3 away from the cavity 4, and a rotor 6 is rotatably connected in the recess 5. In FIG. 6, the rotor 6 has a spherical shape. In some other embodiments, since the rotational direction of the rotor 6 is only in one plane, the rotor 6 may also have a shape of a circular disk. The inner wall of the recess 5 is provided with a radially protruded ring 20 for preventing the rotor 6 from disengaging from the recess 5, and the inner diameter of the protruded ring 20 is smaller than the outer diameter of the rotor 6. An annular groove is circumferentially formed in the side wall of the piston 3, and a sealing ring 21 is embedded in the annular groove. The sealing ring improves the sealing property between the piston 3 and the water inlet chamber 2. Referring to FIG. 7, the sealing ring 21 has a V-shaped cross section, and the V-shaped sealing ring 21 forms a notch, the direction of the notch faces towards the cavity 4 of the water inlet chamber 2. The V-shaped arrangement of the sealing ring 21 enables the sealing ring 21 to have two layers, so as to improve the sealing property of the contact surface between the piston 3 and the water inlet chamber 2. Referring to FIGS. 5 and 6, the rotor 6 is connected with a link 7, an end of the link 7 away from the rotor 6 is connected with an eccentric rotating assembly which drives one end of the link 7 connecting the rotor 6 to reciprocate in the direction of the cavity 4. The eccentric rotating assembly includes a rotating disk 9, an eccentric ring 10, a driving ring 11 and a rotating motor 12. A rotating shaft 13 penetrates through an axial center of the rotating disk 9. The eccentric ring 10 is eccentrically connected to a side surface of the rotating disk 9, and the rotating shaft 13 is located in a space surrounded by the eccentric ring 10. An annular column rotatably connected with the rotating shaft 13 is integrally formed in the eccentric ring 10. Since the rotating shaft 13 itself has been rotatably connected to the rotating disk 9, the arrangement of the annular column mainly maintains the stability of rotatory connection of the rotating disk 9 with the rotating shaft 13. The driving ring 11 is coaxially sleeved outside the eccentric ring 10, the driving ring 11 is connected to the link 7, a conical gear ring 14 is coaxially connected with a side edge of the rotating disk 9, and a driving shaft of the rotating motor 12 is coaxially connected with a conical gear 15 meshed with the conical gear ring 14.

Figure 9:
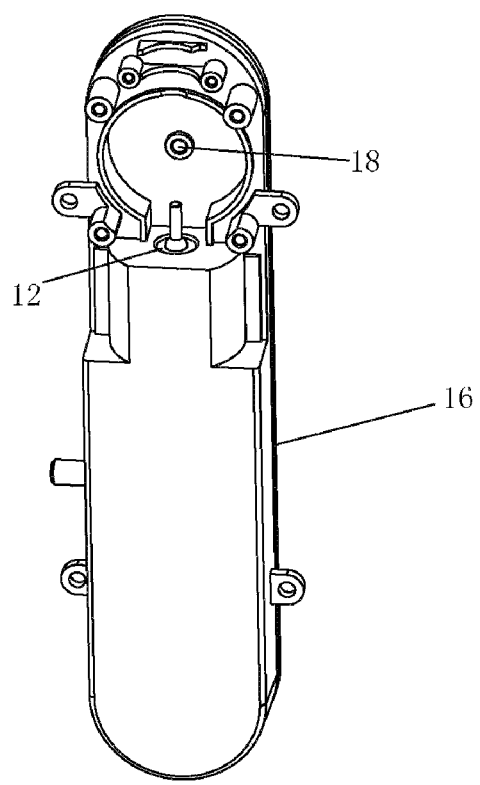
FIG. 9 is a structural schematic diagram of a base according to an embodiment of the present application.

Referring to FIGS. 4 and 9, the ear irrigation device further includes a base 16 and an end cover 17. The base 16 and the end cover 17 are connected to form a cavity enclosing the rotating disk 9, the eccentric ring 10 and the driving ring 11, and protect the cavity of the rotating disk 9, the eccentric ring 10 and the driving ring 11. As shown in FIG. 9, a first pivotal groove 18 is formed in a side surface of the base 16 facing the end cover 17, and the first pivotal groove 18 is surrounded by an annular ring on the base 16. As shown in FIG. 4, a second pivotal groove 19 is formed in a side surface of the end cover 17 facing the base 16, and the second pivotal groove 19 is formed by protruding outward on the end cover 17. Two ends of the rotating shaft 13 abut against an inner bottom wall of the first pivotal groove 18 and an inner bottom wall of the second pivotal groove 19, respectively, and therefore, the first pivotal groove 18 and the second pivotal groove 19 axially limit the rotating shaft 13.

The implementation principle of the ear irrigation device according to the embodiments of the present application is as follows: referring to FIG. 5, the rotating motor 12 drives the conical gear 15 to rotate the meshed conical gear ring 14, so as to rotate the eccentric ring 10 on the rotating disk 9, and the eccentric ring 10 in turn drives the driving ring 11 to move up and down with left and right shaking. The left and right shaking of the driving ring 11 are converted into sliding between the rotor 6 and the recess 5, and the up-down movement of the driving ring 11 are converted into a reciprocating movement of the piston 3 towards the chamber 3. As the piston 3 moves towards the cavity 4, the ball head 33 of the check valve 8 in the water outlet connector 29 is pushed away so that the water in the cavity 4 runs out of the irrigation nozzle 35. When the piston 3 moves in a direction away from the cavity 4, the ball head 33 within the first water inlet connector 22 is pushed away due to the negative pressure within the cavity 4, so that the water in the water reservoir 1 is pumped into the water inlet chamber 2. Due to the reciprocating movement of the piston 3, water in the water inlet chamber 2 intermittently flows out of the irrigation nozzle 35, thereby avoiding the impact of continuous water flow on the external auditory canal.

The above description is only preferred embodiments of the present application and is not intended to limit the protection scope of the present application. Therefore, all equivalent changes of the structure, shape or principle according to the spirit of the present application should be all included in the protection scope of the present application.

What is claimed is:

1. An ear irrigation device, comprising a water reservoir, a water inlet chamber, a water inlet assembly and a water outlet assembly, wherein the water inlet assembly communicates with the water inlet chamber, the water outlet assembly communicates with the water inlet chamber, one end of the water inlet chamber is provided with a slidably engaged piston by insertion, the slidably engaged piston and an interior of the water inlet chamber form a chamber, a recess is formed on a side of the slidably engaged piston facing away from the chamber, a rotor is rotatably connected in the recess, the rotor is connected with a link, an end of the link away from the rotor is connected with an eccentric rotating assembly which drives a second end of the link connected to the rotor to reciprocate in a direction of the chamber, one end of the water inlet assembly communicates with the water reservoir, a first check valve in unidirectional communication with the interior of the water inlet chamber is arranged in the water inlet assembly, a second check valve in unidirectional communication with an outside of the water inlet chamber is arranged in the water outlet assembly, the water inlet assembly comprises a first water inlet connector, a second water inlet connector, a first water inlet pipe, a second water inlet pipe and a closure plug, the first water inlet connector communicates with the water inlet chamber, the first water inlet pipe communicates with the first water inlet connector, one end of the first water inlet pipe away from the first water inlet connector communicates with the second water inlet connector, one end of the second water inlet connector away from the first water inlet pipe is circumferentially sleeved with the closure plug, the closure plug is axially formed with a water passage hole communicating with the first water inlet pipe, the second water inlet pipe is inserted into one end of the water passage hole away from the first water inlet pipe, an open end of the water reservoir is sleeved on a circumferential side wall of the closure plug, one end of the second water inlet pipe away from the closure plug is close to an inner bottom wall of the water reservoir, and the closure plug is axially formed with a ventilation hole communicating with the water reservoir.

2. The ear irrigation device according to claim 1, wherein the eccentric rotating assembly comprises a rotating disk, an eccentric ring, a driving ring and a rotating motor, a rotating shaft penetrates through an axial center of the rotating disk, the eccentric ring is eccentrically connected to a side surface of the rotating disk, the rotating shaft is located in a space surrounded by the eccentric ring, the driving ring is coaxially sleeved outside the eccentric ring, the driving ring is connected to the link, a conical gear ring is coaxially connected with a side edge of the rotating disk, and a driving shaft of the rotating motor is coaxially connected with a conical gear meshed with the conical gear ring.

3. The ear irrigation device according to claim 2, further comprising a base and an end cover, the base and the end cover are connected to form a cavity enclosing the rotating disk, the eccentric ring and the driving ring, a first pivotal groove is formed in a side surface of the base facing the end cover, a second pivotal groove is formed in a side surface of the end cover facing the base, and two ends of the rotating shaft abut against an inner bottom wall of the first pivotal groove and an inner bottom wall of the second pivotal groove, respectively.

4. The ear irrigation device according to claim 1, wherein an inner wall of the recess is provided with a radially protruded ring, and the radially protruded ring abuts against the rotor and prevents the rotor from disengaging from the recess.

5. The ear irrigation device according to claim 1, wherein an annular groove is circumferentially formed in a side wall of the slidably engaged piston, and a sealing ring is embedded in the annular groove.

6. The ear irrigation device according to claim 1, wherein the water outlet assembly comprises a water outlet connector, a first water outlet pipe and a second water outlet pipe, the water outlet connector communicates with the water inlet chamber, the first water outlet pipe communicates with the water outlet connector, and the second water outlet pipe communicates with one end of the first water outlet pipe away from the water outlet connector.

7. The ear irrigation device according to claim 6, wherein one end of the second water outlet pipe away from the first water outlet pipe is detachably connected with an irrigation nozzle.

8. The ear irrigation device according to claim 7, wherein an ear cover is circumferentially connected with a side wall of the irrigation nozzle.

9. The ear irrigation device according to claim 1, wherein the first check valve and the second check valve each comprises a spring, a ball head and a water passage base allowing water to pass through, and two ends of the spring are respectively connected with the water passage base and the ball head.

* * * * *